(12) United States Patent
Wulf

(10) Patent No.: US 6,229,635 B1
(45) Date of Patent: May 8, 2001

(54) LIGHT SENSING DEVICE

(75) Inventor: Jürgen Wulf, Ueberlingen (DE)

(73) Assignee: Bodenseewerk Perkin-Elmer GmbH, Ueberlingen (DE)

(*) Notice: Subject to any disclaimer, the term of this patent is extended or adjusted under 35 U.S.C. 154(b) by 0 days.

(21) Appl. No.: 09/367,951

(22) PCT Filed: Dec. 4, 1997

(86) PCT No.: PCT/DE97/06794
§ 371 Date: Nov. 19, 1999
§ 102(e) Date: Nov. 19, 1999

(87) PCT Pub. No.: WO98/38542
PCT Pub. Date: Sep. 3, 1998

(30) Foreign Application Priority Data

Feb. 24, 1997 (DE) .............................................. 197 07 227

(51) Int. Cl.[7] .................................................. G02B 26/08
(52) U.S. Cl. .......................... 359/196; 359/204; 250/347; 356/318
(58) Field of Search ..................................... 359/196, 212; 250/347, 349; 356/318, 320, 344

(56) References Cited

U.S. PATENT DOCUMENTS 5,304,810 * 4/1994 Amos .................... 250/349

* cited by examiner

Primary Examiner—Darren Schuberg
(74) Attorney, Agent, or Firm—Perman & Green, LLP

(57) ABSTRACT

The present invention relates to a light scanning device for exciting and detecting an emission of secondary light, especially fluorescent light, of a sample, comprising a light generating device for generating scanning light in the form of a single light beam, a deflection unit used for effecting a deflection of the scanning light for scanning at least one subarea of the sample, said deflection being variable in at least one direction, an imaging unit for forming an image of the secondary light emanating from the sample, and a detection unit for detecting the secondary light. When a sample with a large surface to be rastered is subjected to fluorescence examination with high spatial resolution, undesirably long scanning times occur. For reducing the scanning time and for simultaneously maintaining the high resolution in the case of such a sample, the light scanning device according to the present invention comprises a division device for dividing the single light beam into at least two light beams. This has the effect that, instead of the former sequential scanning of the sample, a subdivision into fields is carried out, said fields being scanned simultaneously by the plurality of light beams. The scanning time can therefore be reduced in accordance with the number of the simultaneously scanned fields of the sample.

26 Claims, 3 Drawing Sheets

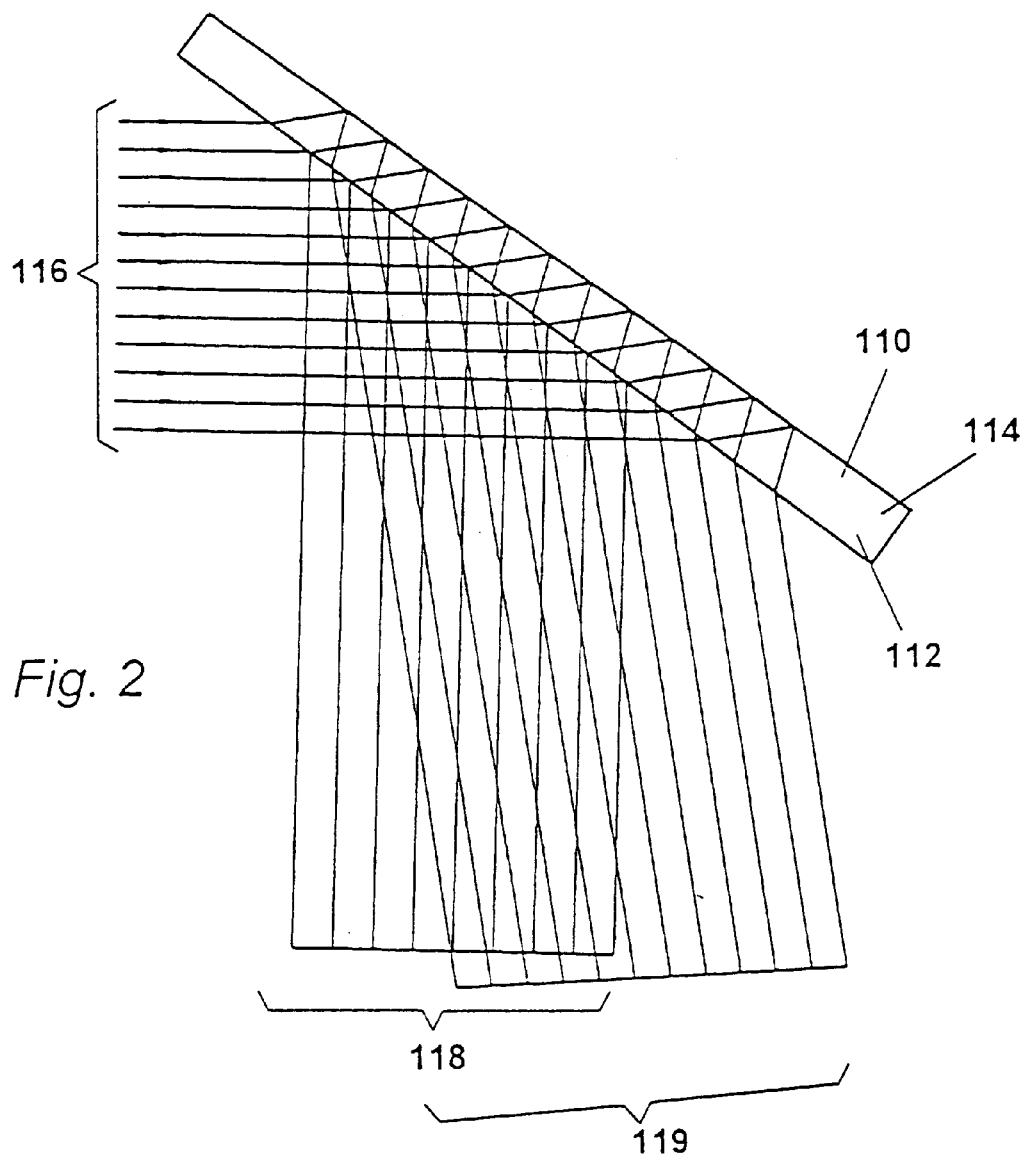
Fig. 2
Fig. 4
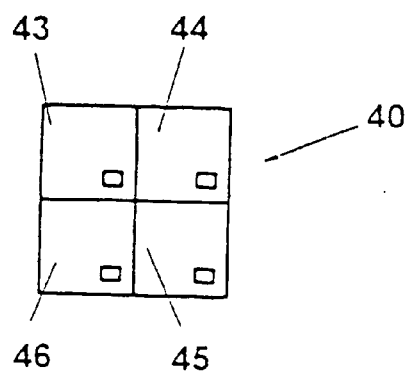

LIGHT SENSING DEVICE

FIELD OF THE INVENTION

The present invention relates to a light scanning device for exciting and detecting an emission of secondary light, especially fluorescent light, of a sample, comprising a light generating device for generating scanning light in the form of a single light beam, a deflection unit used for effecting a deflection of the scanning light for scanning at least one subarea of the sample, said deflection being variable in at least one direction, an imaging unit for forming an image of the secondary light emanating from the sample, and a detection unit for detecting the secondary light.

BACKGROUND ART

Light scanning devices of the above-mentioned type are used e.g. for a spatially resolved fluorescence examination of a sample. For this purpose, the above-mentioned device for generating the scanning light in the form of a single light beam produces a narrow beam, which is focussed onto the sample and which is rastered over the sample by means of a deflection device, e.g. in the form of tilting mirrors with two orthogonal tilting axes or axes of rotation in the optical path of the light beam, said light-generating device being a laser in most cases. The scanning light excites on the surface of a sample the generation of secondary light, e.g. in the form of fluorescent light. This secondary light is collected via an imaging optics and detected on a detection unit. Since the deflection unit irradiates, in a precisely definable manner, a respective specific spot on the sample in dependence upon the position of the tilting mirrors relative to one another and relative to the sample, a locally dependent statement with regard to the respective property of the sample can be made by means of the detection unit detecting the intensity of the secondary light.

The scanning time for measuring the whole sample depends on various parameters, such as the size of the angular field on the sample, the scanning increment, the spot size of the scanning beam on the sample, the integration time of the detection unit, the scanning or mirror velocity of the deflection unit as well as the desired signal-to-noise ratio. When samples with dimensions in the centimeter range are scanned with high spatial resolution by a scanning beam focussed to a few micrometers, the scanning times are in the range of minutes to hours. Such long scanning times are, however, a great problem for the operation of light scanning devices of this kind.

SUMMARY OF THE INVENTION

It is therefore the object of the present invention to provide an improved light scanning device which can be used for scanning a sample and for detecting secondary radiation excited by the scanning light and by means of which a faster and more efficient scanning of a large sample with high spatial resolution can be accomplished.

According to the present invention, this object is achieved by a light scanning device of the type cited at the start, which is characterized in that a division device is provided for dividing the single light beam into at least two light beams. Due to the division of the single light beam into at least two light beams, the whole surface of the sample is no longer scanned sequentially, as has hitherto been the case, but at least two areas of the sample are rastered simultaneously by the at least two scanning beams. Hence, the scanning time can essentially be halved, the spatial resolution remaining the same.

According to an advantageous further development of the present invention, the division device comprises at least one, preferably, however, two wedge-shaped bimirrors, especially beam splitters, comprising each a first and a second surface at which the single incoming beam is reflected, whereby two beams are formed, said two beams enclosing an angle which corresponds to the wedge angle of the beam splitter. When two beam splitters are used in accordance with a preferred embodiment, four beams are produced from the initially single beam. Due to the division of the incoming beam into four beams, the sample is subdivided into four quadrants, whereby the scanning time can essentially be reduced to a quarter of the scanning time required when a single beam is used. The two reflecting, wedge-shaped beam splitters or beam splitters are, advantageously, a part of the deflection unit and represent the respective tilting mirrors with orthogonal axes of rotation of this unit, said tilting mirrors being coupled with suitable adjusting elements.

In accordance with an additional advantageous further development of the present invention, a focussing lens is provided between the deflection unit and the sample. It will especially be of advantage to use an F/Θ lens which focusses the light beams sharply independently of the displacement, i.e. the distance from the optical axis. This kind of arrangement of the focussing lens between the deflection unit and the sample is referred to as "pre-objective-scanning".

According to an additional advantageous further development, the detection unit consists of a spatially resolving detector array, e.g. a CCD camera or a multi-channel multiplier or a multi-channel semiconductor element. For reducing undesired cross-talk between the individual channels, which correspond to the areas on the sample scanned by the individual light beams, a special diaphragm, which is adapted to the respective sample areas scanned, can be provided in front of the detector.

In the case of measurements in a transmissive arrangement, it will be advantageous to provide, if possible, the whole surface behind the sample with light guides, the light guides associated with each scanning area of the sample being combined so as to form a bundle and being conducted to a respective detector area or to a detector of their own. For example, if the sample is subdivided into four quadrants, the light guides are combined so as to form four bundles and are conducted onto four different detectors so that the four quadrants can be measured simultaneously. In this connection it is also possible to arrange colour filters in front of the detectors for suppressing the excitation light on the one hand and for carrying out a selection of the secondary light on the other. The numerical aperture of the light guides restricts the angular field of secondary light emission and prevents therefore cross-talk between the channels. If the sample consists of fluorescent dyes of the same kind, each of the detectors associated with a scanning field of the sample can be equipped with a different colour filter so that, if e.g. four detectors are used, four different emission wavelengths can be measured simultaneously.

Instead of using different detectors coupled to the sample via light-guide bundles, it would also be possible to arrange, according to a further development of the present invention, a CCD camera behind the sample in a transmissive arrangement. For preventing the fluorescent light of all channels from being mixed in the camera, a plate consisting of light-conducting fibres having a small numerical aperture is placed in front of the camera, whereby cross-talk between the channels can be prevented effectively.

According to an additional advantageous further development of the light scanning device according to the present invention, a set-up is provided for detecting the secondary light in a reflective, non-confocal arrangement. For creating said non-confocal arrangement, i.e. for implementing the ray path of the secondary light in such a way that the mirrors of the deflection unit are not included in the ray path of said secondary light, a dichroic beam splitter is advantageously provided between the deflection unit and the sample, said dichroic beam splitter being adapted to be used for separating the optical path of the scanning light from the optical path of the secondary light emanating from the sample. Especially, the dichroic beam splitter transmits the excitation light having a first shorter wavelength, whereas it reflects the secondary light having a longer wavelength.

Further advantageous embodiments are disclosed by the sub-claims.

BRIEF DESCRIPTION OF THE DRAWINGS

Making reference to the accompanying drawings, the present invention will be explained and described in more detail on the basis of a preferred embodiment serving as an example.

In the said drawings,

FIG. 2 shows an example of the division device in the form of a wedge-shaped beam splitter plate with a suitable ray path;

FIG. 4 shows a sketch for illustrating the subdivision of a sample into four quadrants.

DETAILED DESCRIPTION OF THE PREFERRED EMBODIMENT

Figure 1:
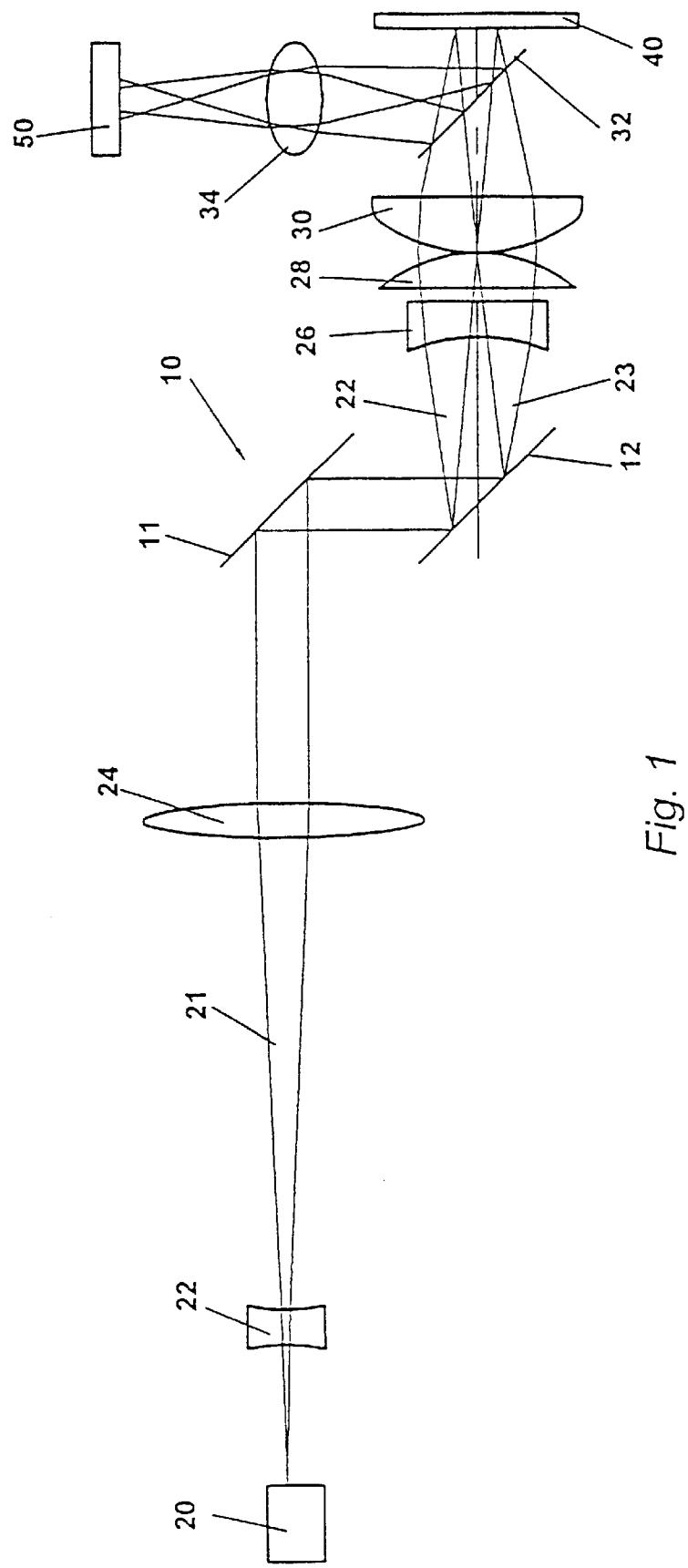
FIG. 1 shows a sketch for illustrating the fundamental set-up and the ray path of a light scanning device according to the present invention.

FIG. 1 shows, by way of example, a schematic set-up of a light scanning device according to the present invention. In a light-generating device 20, e.g. a laser, a single light beam 21 having a specific wavelength is produced. The light beam produced by the light-generating device or rather the laser is spatially filtered in a spatial filter in an advantageous manner, said spatial filter being not shown. The bundle of parallel rays is expanded by means of an expansion optics comprising e.g. two lenses 22 and 24, so as to form a beam having a larger cross-section, said beam being again a bundle of parallel rays. The next element following in the optical path is a deflection unit 10 comprising tilting mirrors 11 and 12 which have orthogonal axes of rotation and which are connected to adjusting elements, not shown, provided with suitable control means for adjusting or tilting said tilting mirrors relative to one another so as to raster the beam 21 in two directions. As will be explained in detail hereinbelow with regard to FIG. 2, the tilting mirrors 11 and 12 each consist of reflecting, wedge-shaped beam splitters or beam splitter plates in an advantageous embodiment of the present invention, said reflecting beam splitters or beam splitter plates defining consequently a division device for dividing the single incoming laser beam into a total of four separate laser beams. For reasons of clarity, only two beams 22 and 23 are shown in FIG. 1.

Between the deflection unit 10 comprising the tilting mirrors 11 and 12, a focussing optics is arranged, which comprises e.g. a triplet lens consisting of the lenses 26, 28 and 30. This focussing optics consists advantageously of an F/Θ lens which, indpendently of the displacement, focusses the beam sharply to spot sizes in the micrometer range on a sample 40. When an F/Θ lens is used, the scanning beams are imaged according to the so-called F/Θ condition y'=F/Θ, wherein y' is the imaging coordinate, F the focal length and e the angle enclosed by the scanning beam and the optical axis. In contrast to conventional lenses, where the normally applicable condition y'=F×tan Θ holds true, the F/Θ lens causes barrel distortion. This, however, guarantees a porportionality between the scanning angle and the image height y' and simultaneously also a proportionality between the angular velocity of the deflection system and the scanning velocity in the sample plane. It follows that, when the angular velocity for the deflection of the beam is constant, a constant excitation intensity on the sample will be created, independently of the scanning position, due to the linearity between the scanning velocity on the sample and the angular velocity.

This kind of arrangement of the focussing optics between the deflection unit 10 comprising the tilting mirrors 11 and 12 and the sample 40 is referred to as "pre-objective scanning". This is used more frequently than "post-objective scanning" where the focussing optics is arranged in the optical path in front of the deflection unit 10 so that the scanning light, which is convergent after the focussing optics, is deflected via the deflection mirrors and directed onto the sample 40. In the case of this kind of arrangement of the focussing optics in front of the deflection unit 10, the lens only has to fulfil minimal demands. It may have a small diameter and it only has to form sharp images in the paraxial region. The deflection unit arranged behind the lens results, however, in a curved scanning line located on a circular arc about the axis of rotation of the tilting mirror. This "post-objective scanning" arrangement is therefore not preferred for scanning plane surfaces.

Hence, it will be advantgeous to use the "pre-objective scanning" arrangement comprising an F/Θ lens, which can be used for forming images in a plane with an image coordinate that is proportional to the deflection angle. The F/e lens in the "pre-objective scanning" arrangement must, however, have a comparatively large diameter so that it will also accept scanning beams having a large scanning angle. It must also be corrected over a comparatively large angular field according to the tilting of the light beam relative to the axis and, in addition, it must have a good field flatness.

A dichroitic mirror 32 is arranged between the focussing optics and the sample 40, said dichroic mirror 32 permitting passage of the excitation light having the specific wavelength and reflecting the secondary light which is generated on or by the sample 40 and which has a wavelength that is different from, i.e. longer than that of the excitation light. In the reflection direction of the dichroic mirror 32 a collecting optics 34 and a detector 50 are arranged after said dichroic mirror.

The arrangement shown in FIG. 1 represents a case in which the secondary light is measured in a reflective, non-confocal arrangement. The non-confocal arrangement has the advantage that a larger solid angle for the secondary light emitted by the sample can be accepted than in the case of confocal imaging.

Notwithstanding this, also a confocal arrangement (not shown in FIG. 1) would be possible in contrast thereto; in such a confocal arrangement, the secondary light emitted by the sample is guided back via the same tilting mirrors 11 and 12 so that the light travels along a ray path which corresponds exactly to that of the scanning light but in the opposite direction. In this arrangement, the dichroic mirror would be provided between the light source 20 and the deflection unit 10 so as to separate the optical paths of the excitation light and of the wavelength-displaced secondary light. By additionally focussing the secondary light onto a pinhole diaphragm (not shown), e.g. a pinhole diaphragm having a hole in the micrometer range, undesired stray light could be suppressed to a large extent. The confocal arrangement, however, only accepts a very small solid angle of the secondary light, which is limited by the mirror apertures, when a comparatively large angular field is to be scanned simultaneously.

In contrast to the arrangement shown in FIG. 1, it would also be possible to measure in a transmissive arrangement instead of a reflective arrangement. In a transmissive arrangement, the scanning and excitation light, respectively, must be blocked with the aid of filters (not shown) (e.g. notch filters or cut-off filters), which, in turn, reflect light onto the sample and which therefore cause blurring of the excitation light spot on the sample. Hence, the reflective arrangement shown in FIG. 1 is advantageous in comparison with the transmissive arrangement.

FIG. 2 shows in the form of an example how the division device for dividing the single light beam into at least two light beams can be realized according to the present invention. The division device consists of a wedge-shaped beam splitter plate 110, the respective light rays of an incident light beam 116 being reflected on the first surface 112 and on the second surface 114 of said beam splitter plate 110 so as to produce two light beams 118 and 119. It will be advantageous when the tilting mirror 12 shown in FIG. 1 is implemented in the form of the wedge-shaped beam splitter plate 110 shown in FIG. 2. In particular, it will be advantageous when each of the two tilting mirrors 11 and 12 of the deflection unit 10 in FIG. 1 is implemented in the form of a beam splitter plate 110 of the kind shown in FIG. 2, whereby the single incident light beam will be divided into four light beams. In this case, the sample 40 is subdivided into four quadrants 43, 44, 45 and 46 as shown in FIG. 4. The area of each quadrant of the sample is therefore scanned by one of the four beams of the scanning light by means of adjusting the tilting mirrors in a suitable manner. It follows that, when a sample having macroscopic dimensions of approx. 24×24 mm is scanned, the time required for complete scanning of this sample will be reduced to a quarter of the hitherto necessary time. It is therefore possible to focus the scanning light beams more strongly than has hitherto been the case so as to increase the spatial resolution in the scanning process, the time required for scanning a large sample being still acceptable.

When the scanning light beam is focussed onto a point, stray light can also reach neighbouring molecules whose secondary light will, in the case of non-focal imaging, be included in the measurement and associated with the instantaneous position of the tilting mirrors of the scanning unit. Notwithstanding this, a non-confocal set-up could still be of advantage, since, when a confocal set-up is used, the signal is much smaller due to the smaller solid angle. In addition, the above-mentioned difficulty with regard to stray light is reduced by the arrangement according to the present invention, since an increase in the resolution, i.e. stronger focussing of the scanning beam without a resultant increased expenditure of time for the scanning of the sample, is possible.

A further advantage of the embodiment described is to be seen in the fact that, due to the division of the scanning light beam into four light beams and due to a corresponding division of the sample into four quadrants, each of the scanning light beams only has to cover a smaller area. Hence, only minor deflections of the tilting mirrors 11 and 12 are required, which can be realized with smaller errors and tolerances, respectively. The tilting movements of the tilting mirrors are adapted in such a way that the quandrants 43–46 shown in FIG. 4 are each swept completely by the respective sub-beams.

The wedge angle of the beam splitter plates is, in an advantageous manner, large enough to make the macroscopic distance between the individual beams on the sample large in comparison with the mean scattering length within the sample. In the case of an exemplary sample having an area of 24×24 mm, this distance has an optimum value of 12 mm.

Figure 3:
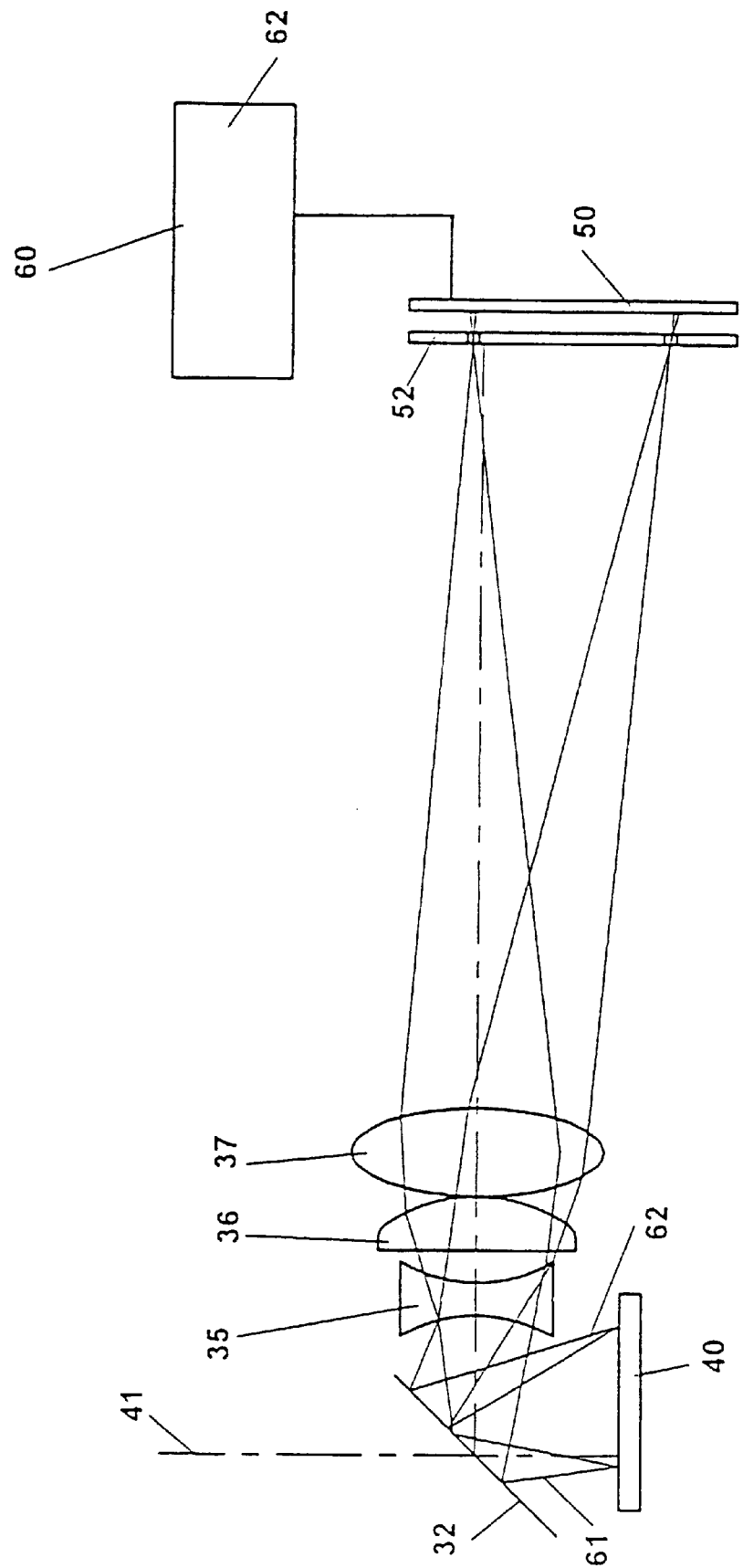
FIG. 3 shows a sketch for illustrating the various detection channels in a light scanning device according to the present invention.

FIG. 3 shows schematically the fundamental structural design of the various detection channels. Secondary light, which is shown in the form of beams 61 and 62, is generated at two points of the sample 40. As has already been mentioned, this light is reflected at the dichroic mirror 32 and is then focussed onto the detector 50 through a macrolens consisting e.g. of three lenses 35, 36 and 37. Each point of the sample plane corresponds unequivocally to a point in the detector plane. The detector is advantageously a CCD camera or a multi-channel photomultiplier, e.g. the model R5900U-00-M4 by Hamamatsu, or a multi-channel semiconductor element. Detectors of this kind are suitable for simultaneously detecting a plurality of channels. The respective scanning fields of the sample (e.g. four quadrants) are correspondingly imaged on the detector plane. For suppressing an undesirable cross-talk between the channels, a special diaphragm 52, which is adapted to the subdivision of the sample, can be provided in front of the detector 50. For the above-mentioned embodiment with four scanning light beams, the diaphragm 52 is subdivided into four quandrants in a corresponding manner.

In contrast to the arrangement for measuring the secondary light in reflection, which is shown in FIG. 1 and 3, it is also possible to measure in a transmissive arrangement. In such a transmissive arrangement, e.g. the whole surface behind the sample is provided with light guides, the light guides of each quadrant being combined so as to form one bundle. Four bundles are then conducted onto four different detectors which can be measured simultaneously. For suppressing the excitation light and for selecting the secondary light, special filters can be provided in front of the detectors. The numerical aperture of the light guides restricts the angular field of secondary light emission and prevents therefore cross-talk between the channels. If the sample consists of fluorescent dyes of the same kind, each of the detectors associated with a quadrant can be equipped with a different colour filter so that up to four different emission wavelengths can be measured simultaneously. Alternatively, a CCD camera can simply be provided behind the sample. This camera would, however, mix the fluoresent light of all four channels. This is prevented by positioning a plate (a so-called face plate) consisting of light-conducting fibres having a small numerical aperture in front of the camera so as to suppress cross-talk between the channels.

What is claimed is:

1. A light scanning device for exciting and detecting an emission of secondary light by a sample, comprising:
   a light generating device for generating scanning light in the form of a single light beam,
   a deflection unit used for effecting a deflection of the scanning light for scanning at least one subarea of the sample, said deflection being variable in at least one direction, an imaging unit for forming an image of the secondary light emanating from the sample, a detection unit for detecting the secondary light, and a division device in the optical path of the scanning light for dividing the single light beam into at least two light beams, each of the light beams having the same spectral qualities as the single beam.

2. The light scanning device according to claim 1, wherein the division device is a reflecting wedge-shaped beam splitter with first and second surfaces which form an angle with each other and at which the single light beam is reflected, whereby two light beams enclosing the same angle with each other are formed.

3. The light scanning device according to claim 2, wherein the division device comprises two wedge-shaped bimirrors which are arranged so that the single light beam is reflected at the first reflecting, wedge-shaped beam splitter, whereby two light beams are formed which impinge upon the second reflecting, wedge-shaped beam splitter and which are reflected at this second reflecting beam splitter, whereby four light beams are formed.

4. The light scanning device according to claim 3, wherein the two reflecting, wedge-shaped beam splitters constitute part of the deflection unit and are connected to adjusting elements for rotating and/or displacing the respective bimirrors for scanning the sample.

5. The light scanning device according to claim 1, wherein a focussing optics is provided between the division device and the sample for focussing all light beams onto the sample.

6. The light scanning device according to claim 5, wherein the focussing optics comprises an F/θ lens.

7. The light scanning device according to claim 1, wherein the detection unit is implemented so that it is suitable for detecting the secondary light in a spatially resolved manner.

8. The light scanning device according to claim 7, wherein the detection unit is subdivided into fields in correspondence with the number of scanning light beams impinging upon the sample.

9. The light scanning device according to claim 8, wherein a diaphragm subdivided in correspondence with the fields of the detection unit is arranged in front of said detection unit.

10. The light scanning device according to claim 1, wherein the imaging unit is arranged so that it is adapted to accept secondary light transmitted by the sample.

11. The light scanning device according to claim 10, wherein on a side of the sample located opposite a side where the scanning light is incident, light guides arranged to form a bundle and which are subdivided into sub-bundles at their detector-side end according to respective scanning areas of the scanning light beams impinging upon the sample, each of said sub-bundles having associated therewith detectors of their own.

12. The light scanning device according to claim 11, wherein respective wavelength filters are disposed between the sub-bundles of light guides and the respective detectors.

13. The light scanning device according to claim 12, wherein the wavelength filters are colour filters for the respective different wavelengths of the secondary light.

14. The light scanning device according to claim 10, wherein the imaging unit is a plate comprising light-conducting fibres having a small numerical aperture and wherein the detection unit comprises a CCD camera.

15. The light scanning device according to claim 1, wherein an arrangement for detecting the secondary light is a reflective, non-confocal arrangement.

16. The light scanning device according to claim 15, wherein the imaging unit comprises a dichroic beam splitter by means of which the optical path of the scanning light can be separated from that of the secondary light emanating from the sample.

17. The light scanning device according to claim 1, wherein the light generating device used for generating the scanning light in the form of a single beam comprises a laser.

18. The light scanning device according to claim 1, wherein the light-generating device used for generating the beam comprises a device for spatially filtering the single beam.

19. The light scanning device according to claim 1, wherein the single light beam and each light beam divided from the single light beam have a specific wavelength.

20. A light scanning device for exciting and detecting an emission of secondary light by a sample, comprising:

a light generating device for generating scanning light in the form of a single light beam, a deflection unit used for effecting a deflection of the scanning light for scanning at least one subarea of the sample, said deflection being variable in at least one direction, an imaging unit for forming an image of the secondary light emanating from the sample, a detection unit for detecting the secondary light, and a division device in the optical path of the scanning light for dividing the single light beam into at least two light beams, the division device being a reflecting wedge-shaped beam splitter with first and second surfaces which form an angle with each other and at which the single light beam is reflected, whereby two light beams enclosing the same angle with each other are formed.

21. The light scanning device according to claim 20, wherein the division device comprises two wedge-shaped bimirrors which are arranged so that the single light beam is reflected at the first reflecting, wedge-shaped beam splitter, whereby two light beams are formed which impinge upon the second reflecting, wedge-shaped beam splitter and which are reflected at this second reflecting beam splitter, whereby four light beams are formed.

22. The light scanning device according to claim 21, wherein the two reflecting, wedge-shaped beam splitters constitute part of the deflection unit and are connected to adjusting elements for rotating and/or displacing the respective bimirrors for scanning the sample.

23. A light scanning device for exciting and detecting an emission of secondary light by a sample, comprising:

a light generating device for generating scanning light in the form of a single light beam, a deflection unit used for effecting a deflection of the scanning light for scanning at least one subarea of the sample, said deflection being variable in at least one direction, an imaging unit for forming an image of the secondary light emanating from the sample, a detection unit for detecting the secondary light, a division device in the optical path of the scanning light for dividing the single light beam into at least two light beams, and wherein on a side of the sample located opposite a side where the scanning light is incident, light guides arranged to form a bundle and which are subdivided into sub-bundles at their detector-side end according to respective scanning areas of the scanning light beams impinging upon the sample, each of said sub-bundles having associated therewith detectors of their own.

24. The light scanning device according to claim 23, wherein respective wavelength filters are disposed between the sub-bundles of light guides and the respective detectors.

25. The light scanning device according to claim 24, wherein the wavelength filters are colour filters for the respective different wavelengths of the secondary light.

26. The light scanning device according to claim 23, wherein the imaging unit is a plate comprising light-conducting fibres having a small numerical aperture and wherein the detection unit comprises a CCD camera.

* * * * *